(12) United States Patent
Faulhaber

(10) Patent No.: US 10,499,955 B2
(45) Date of Patent: *Dec. 10, 2019

(54) SELF IN-FUSING PEDICLE SCREW IMPLANT

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 37 days.

This patent is subject to a terminal disclaimer.

(21) Appl. No.: 15/866,511

(22) Filed: Jan. 10, 2018

(65) Prior Publication Data
US 2018/0125535 A1 May 10, 2018

Related U.S. Application Data

(63) Continuation of application No. 14/831,980, filed on Aug. 21, 2015, now Pat. No. 9,895,169.

(51) Int. Cl.
*A61B 17/70* (2006.01)
*A61B 17/88* (2006.01)
*A61B 17/16* (2006.01)
*A61B 17/86* (2006.01)

(52) U.S. Cl.
CPC ...... *A61B 17/7032* (2013.01); *A61B 17/1671* (2013.01); *A61B 17/7035* (2013.01); *A61B 17/7037* (2013.01); *A61B 17/7044* (2013.01); *A61B 17/7082* (2013.01); *A61B 17/8605* (2013.01); *A61B 2017/8655* (2013.01)

(58) Field of Classification Search
CPC ............ A61B 17/7032; A61B 17/1671; A61B 17/7035; A61B 17/7037; A61B 17/7044; A61B 17/7082; A61B 17/8605; A61B 2017/8655
USPC ......... 606/79, 80, 82, 84, 85, 265, 266, 267, 606/268, 270, 271, 272, 279, 305, 307, 606/308, 310, 314, 319, 99, 104, 86 A
See application file for complete search history.

(56) References Cited

U.S. PATENT DOCUMENTS

| | | | | |
|---|---|---|---|---|
| 5,484,437 A | * | 1/1996 | Michelson | A61B 17/1671 128/898 |
| 5,632,747 A | * | 5/1997 | Scarborough | A61B 17/1637 408/209 |
| 5,797,917 A | * | 8/1998 | Boyd | A61B 17/1637 606/179 |
| 5,899,905 A | * | 5/1999 | Errico | A61B 17/7032 606/256 |
| 7,553,313 B2 | * | 6/2009 | Bagby | A61B 17/025 606/279 |
| 7,722,650 B2 | | 5/2010 | Ashman | |
| 8,740,946 B2 | | 6/2014 | Peterson et al. | |
| 8,998,968 B1 | | 4/2015 | Brow | |

(Continued)

*Primary Examiner* — Pedro Philogene
*Assistant Examiner* — David C Comstock

(57) ABSTRACT

An anchoring system implantable in bone. The anchoring system includes a screw having a screw head, a screw shaft, a plurality of interface elements, each adjacent pair of the interface elements has an interface by-pass channel disposed therebetween, a boring ring that includes cutting teeth and a ring by-pass channel, and a coupling assembly that is adjustable with respect to a longitudinal axis of the screw.

18 Claims, 18 Drawing Sheets

(56) References Cited

U.S. PATENT DOCUMENTS

| | | | |
|---|---|---|---|
| 2007/0123909 A1* | 5/2007 | Rupp | A61B 17/92 606/104 |
| 2007/0149980 A1* | 6/2007 | Seedhom | A61B 17/1637 606/99 |
| 2010/0094356 A1* | 4/2010 | Varela | A61B 17/862 606/304 |
| 2010/0152787 A1* | 6/2010 | Walsh | A61B 17/7037 606/308 |
| 2011/0190821 A1 | 8/2011 | Chin et al. | |
| 2011/0313466 A1* | 12/2011 | Butler | A61B 17/7064 606/279 |
| 2012/0172932 A1 | 7/2012 | Biedermann et al. | |
| 2013/0018428 A1 | 1/2013 | Harper et al. | |
| 2013/0338715 A1 | 12/2013 | Daly et al. | |
| 2014/0288601 A1* | 9/2014 | Baynham | A61B 17/7064 606/247 |
| 2015/0032162 A1 | 1/2015 | Biedermann et al. | |
| 2015/0157377 A1* | 6/2015 | Pham | A61B 17/7055 606/279 |

* cited by examiner

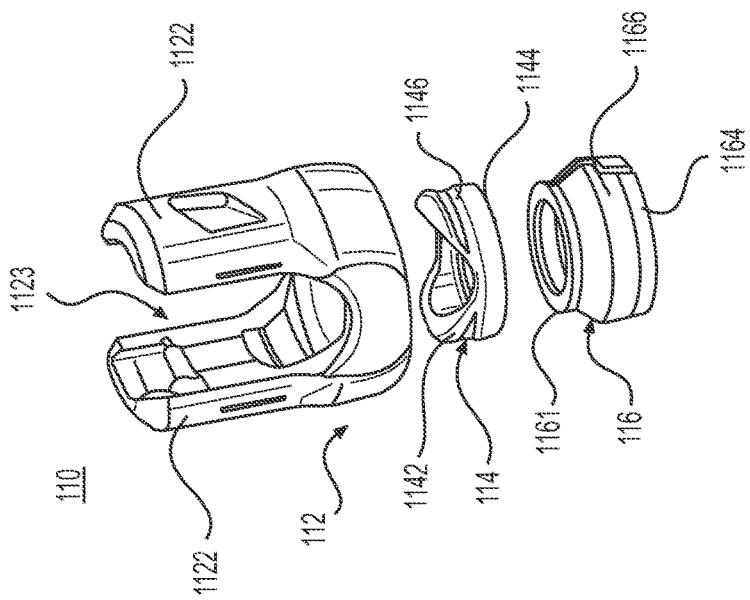
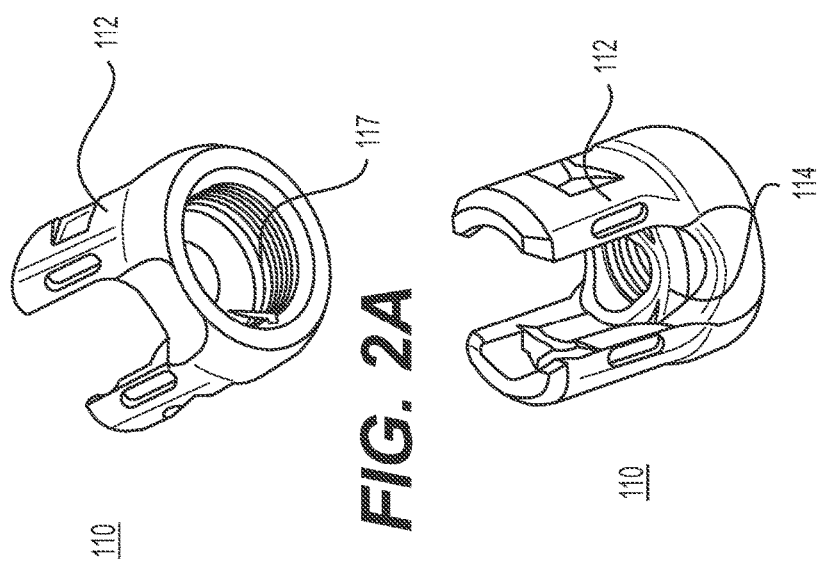

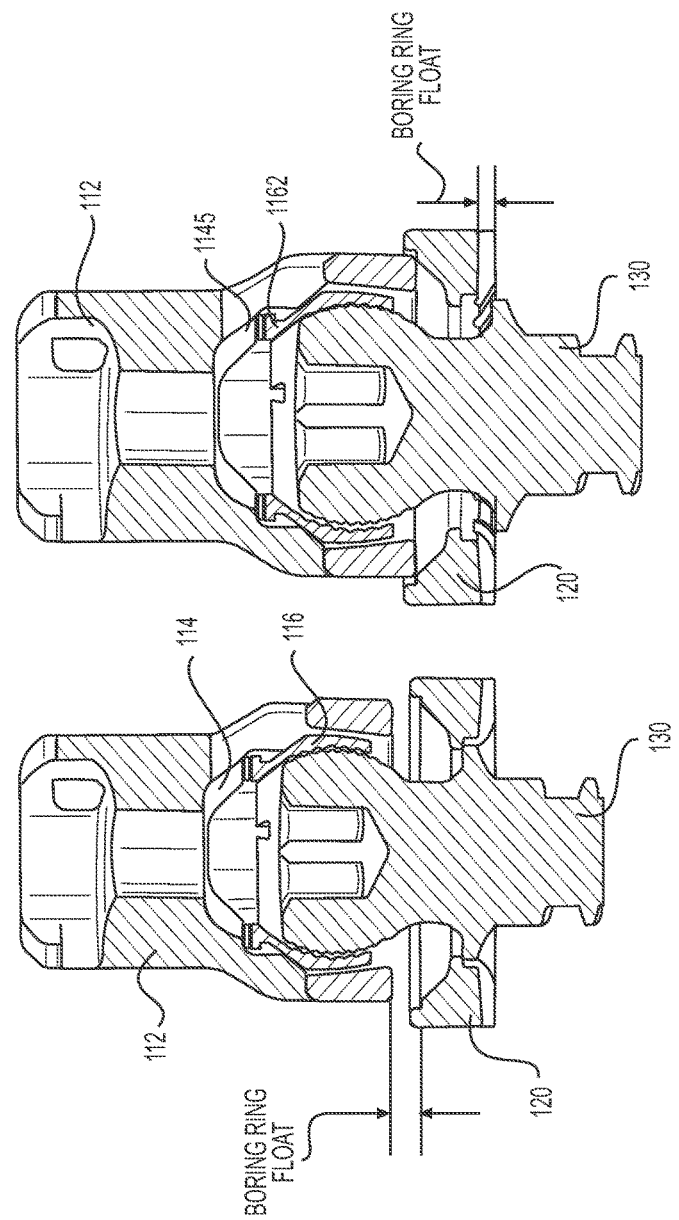

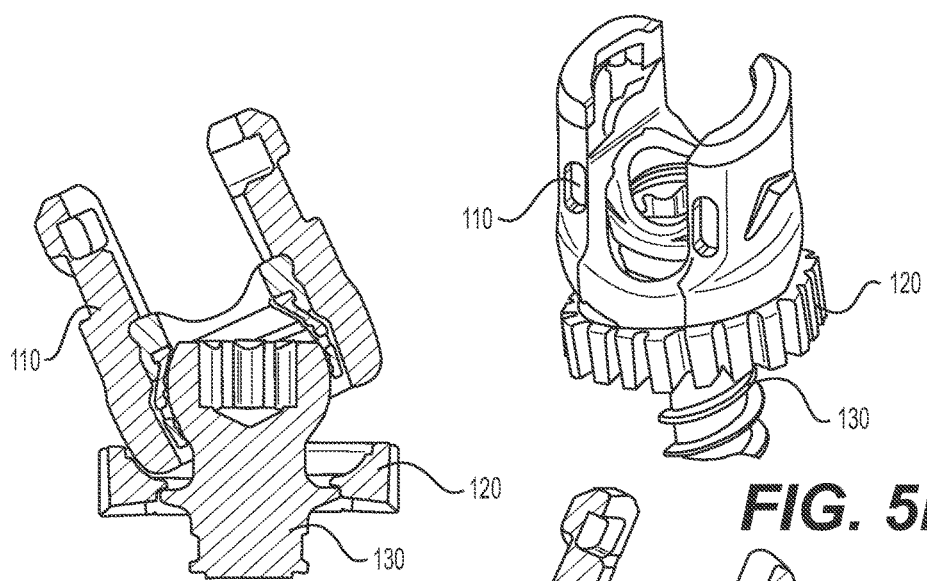
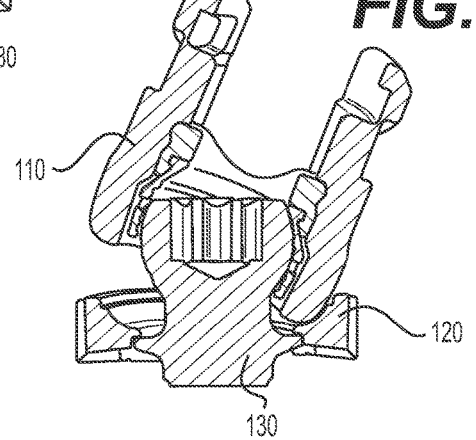
FIG. 5C
FIG. 5E
FIG. 5D

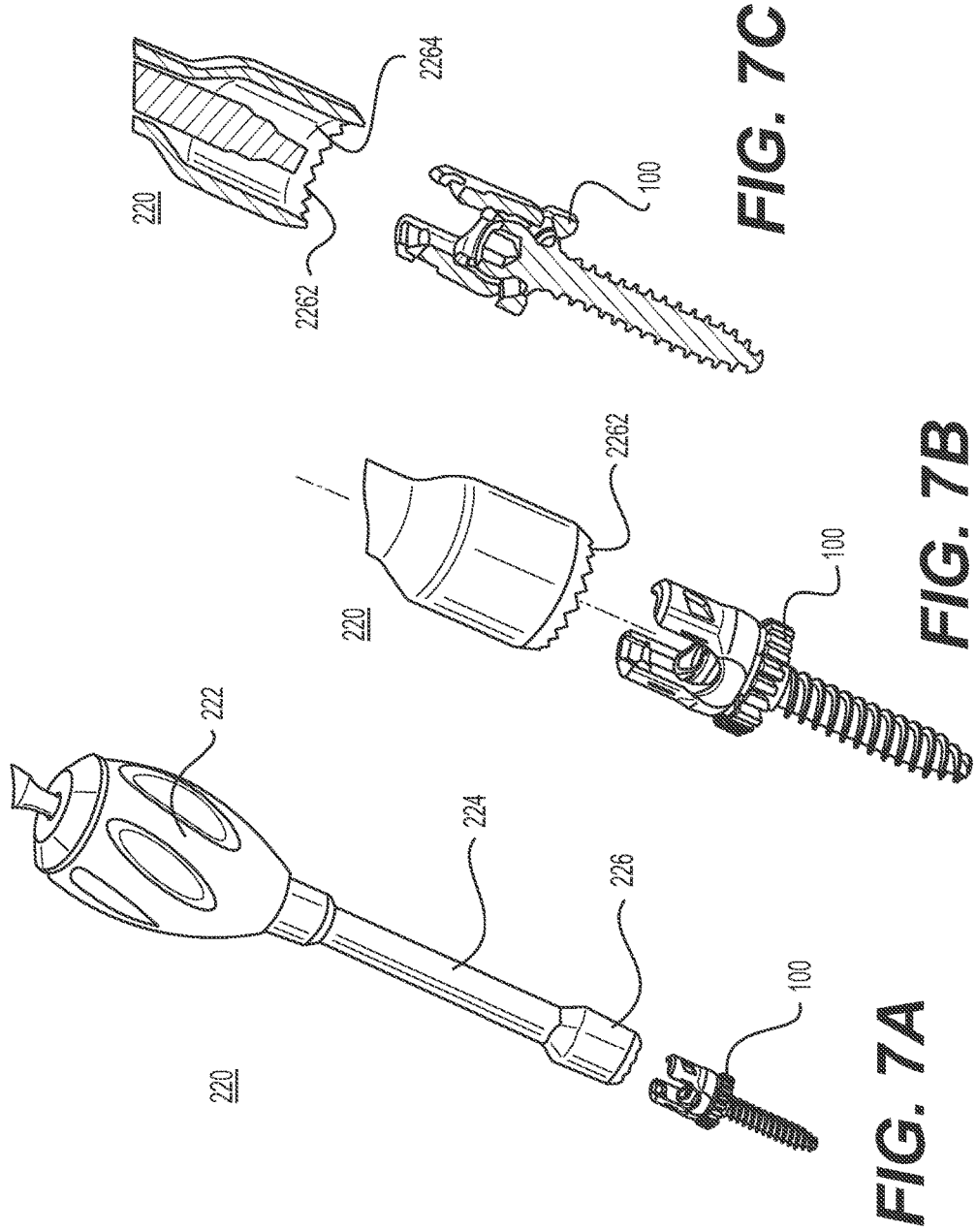

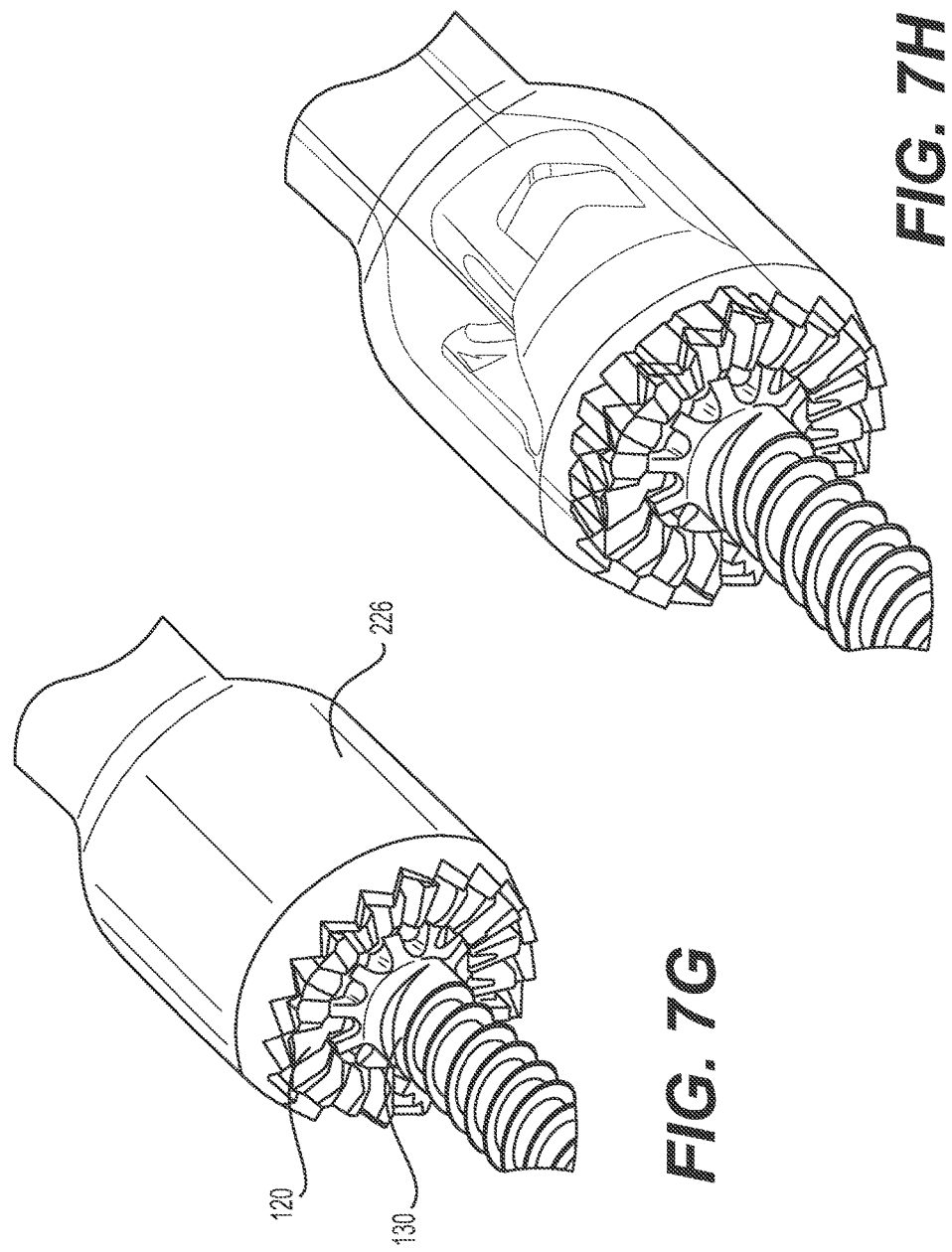

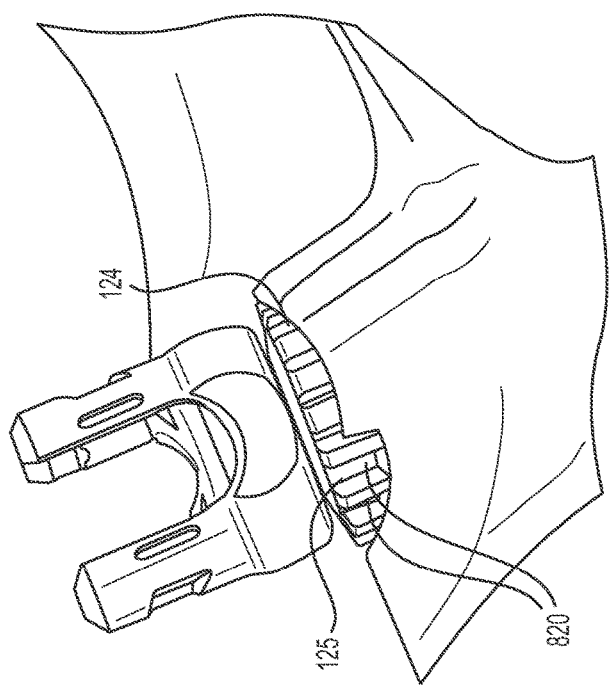
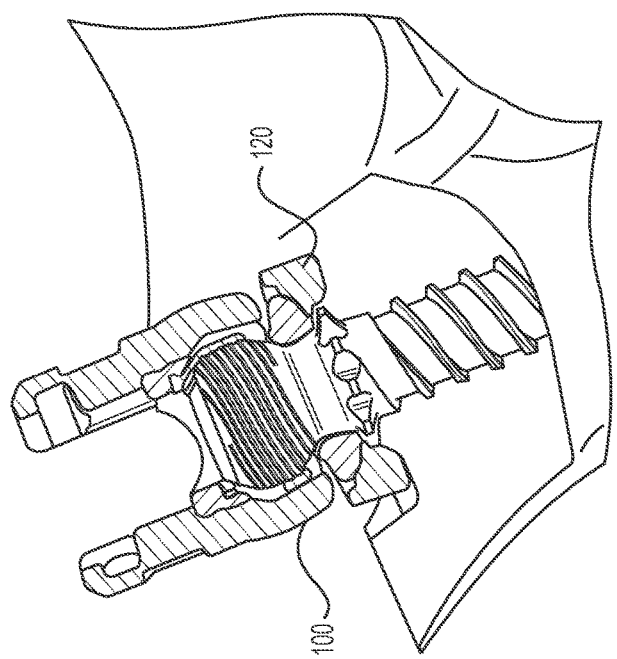
FIG. 9A
FIG. 9B

SELF IN-FUSING PEDICLE SCREW IMPLANT

CROSS REFERENCE TO RELATED APPLICATIONS

This application is a continuation of U.S. patent application Ser. No. 14/831,980, filed Aug. 21, 2015, which is incorporated by reference herein in its entirety for all purposes.

FIELD OF THE DISCLOSURE

The present disclosure relates to bone fixation devices that may include a rod and a bone screw with a variable angle coupling element; and, more particularly, to an anchoring system that aids in the correction of, for example, posterior segmental fusion by adding or facilitating the addition of a bone graft to an implant site.

BACKGROUND OF THE DISCLOSURE

Often, severe pain or damage to the nervous system is caused by spinal abnormalities. Also, movement of the spinal column may be significantly limited by such abnormalities. Many of these abnormalities may be the result of, for example, trauma or degenerative disc disease. Known treatments of such abnormalities typically involve affixing screws or hooks to one or more vertebrae and connecting the screws or hooks to a rod that is aligned with the longitudinal axis of the spinal column to immobilize the spinal segments with respect to each other. Pedicle screw systems are frequently used to provide spinal fixation.

A number of pedicle screw systems are known, which share common techniques and principles of screw placement and rod attachment. Generally, bone screws are screwed into pedicles of vertebrae and coupled to at least one elongated rod. The pedicles, which consist of a strong shell of cortical bone and a core of cancellous bone, are generally used for the bone screw sites because they provide the strongest point of attachment of a spine and, thereby, the greatest resistance against bone-metal junction failure. The bone screws may be positioned so as to traverse all three columns of the vertebrae, thereby providing ventral and dorsal stability in the spine.

Known pedicle screw systems typically include pedicle screws and rods to stabilize adjacent spinal segments. Such systems also include variable angled coupling caps (or heads) on the pedicle screws to allow for angular adjustment of the coupling mechanism between the rod and screws. Since pedicle size and angulation varies throughout the spinal column, several different sizes and shapes of pedicle screws are used in these systems. These systems are generally designed to provide stable and rigid structures to promote bone growth and fusion.

Recovery from spinal surgery is typically a long and arduous process that places severe restrictions on patient mobility. Accordingly, a continuing need exists for systems and methodologies that improve patient recovery and reduce recovery time after surgery.

SUMMARY OF THE DISCLOSURE

The present disclosure is generally directed towards an improved anchoring system that, among other things, aids in correction of posterior segmental fusion by adding a bone graft to an implant construct, promoting fusion. Exemplary embodiments of the anchoring system may include a bone screw system that decorticates, promotes bleeding and promotes creation of a bone graft composition at a base of the implantation that will infuse and solidify itself to, for example, the pedicle and the inferior side of a bone screw during the healing process. The system also provides an optimal surface area of fusion under a screw, which decreases the chance of a "windshield-wiper effect" that is sometimes observed in practice with conventional pedicle screws, thereby reducing any chance of screw pullout.

According to an exemplary embodiment of the disclosure, an anchoring system for implanting in bone is disclosed. The anchoring system comprises a screw assembly that includes a screw head, a screw shaft and a plurality of interface elements. The screw assembly may further include a boring ring that includes cutting teeth and ring by-pass channels. The anchoring system may further comprise a coupling assembly. The screw assembly may comprise a neck portion located between the screw head and the plurality of interface elements. The neck portion may be configured to receive tissue, blood or bone to promote graft formation.

The interface elements may include interface by-pass channels located therebetween. The interface elements may extend radially from the screw in a direction that is substantially normal to the longitudinal axis of the screw. The interface elements may comprise a tapered surface.

The boring ring may be configured to float between the plurality of interface elements and the coupling assembly. The boring ring may comprise an annular portion that facilitates polyaxial angulation, pivoting or rotation of the coupling assembly. The boring ring may comprise a wall portion that has one or more flat portions that are configured to interface with a boring driver.

The coupling assembly may be adjustable with respect to a longitudinal axis of the screw. The coupling assembly may include a coupling body that receives and holds an elongate rod. The coupling assembly may further include a clamp that couples the coupling body to the screw head. The coupling assembly may include a saddle that attaches to the clamp.

According to another exemplary embodiment of the disclosure, a driver assembly is disclosed. The driver assembly may include a screw driver and a boring driver. The screw driver and boring driver may be used separately. The boring driver may include a longitudinal channel that is configured to receive and guide the screw driver to engage the head portion of the screw assembly in an anchoring system. The boring driver may include a handle, a driver shaft, and a driver head. The driver head may include teeth (or serrations) at its distal end, which may be configured to cut into tissue and bone. The driver head may have a cavity that is configured to receive the coupling assembly and boring ring of the anchoring system. The driver head may include a plurality of engaging interfaces that are configured to contact and engage corresponding portions of the ring, thereby engaging and substantially locking the boring ring in place with respect to the driver head, so that when the handle is turned under force of hand and the driver head rotates resultantly, the boring ring is caused to rotate simultaneously.

The driver head may be configured to envelope the entirety of the coupling assembly and the boring ring of the anchoring system. The driver head may include a ring stop to prevent the boring ring from going too deep into the cavity and to maintain the boring ring in an optimal position to cut into bone by exposing the entirety (or a portion) of the cutting teeth on the lower portion of the boring-ring. The driver head may be configured to allow the boring ring to float along the longitudinal axis of the screw assembly.

Additional features and utilities of the exemplary embodiments described herein may be set forth or apparent from consideration of the detailed description and drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to help explain the principles of the disclosure. No attempt is made to show structural details of the disclosure in more detail than may be necessary for a fundamental understanding of the disclosure and the various ways in which it may be practiced. In the drawings:

FIGS. 2A-2C show various views of an exemplary embodiment of a coupling assembly that may be included in the anchoring system of FIG. 1;

FIGS. 5A-5E show various partial views of a portion of the exemplary embodiment of the anchoring system in FIG. 1;

FIGS. 7A-7H show various views of the bore driver engaging and driving the anchoring system of FIG. 1;

FIGS. 9A-9D show various views of the exemplary anchoring system after it has been implanted in a bone.

Figure 1:
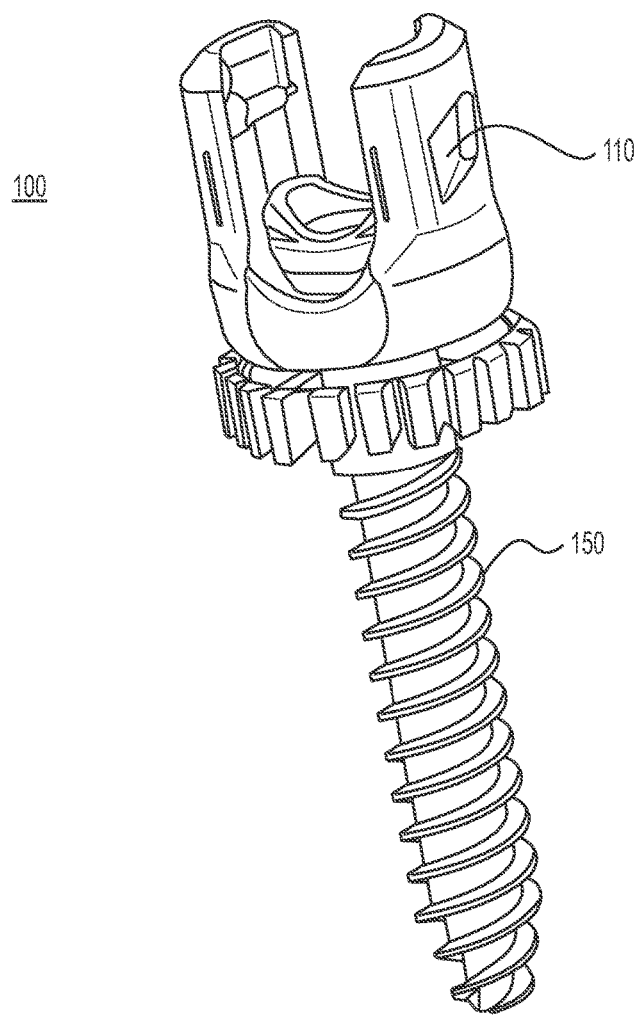
FIG. 1 shows an exemplary embodiment of an anchoring system.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

FIG. 1 shows an embodiment of an anchoring system 100. The anchoring system 100 comprises a coupling assembly 110 and a screw assembly 150. The coupling assembly 110 is configured to pivot about and attach to a head portion (shown in FIG. 3C) of the screw assembly 150. The coupling assembly 110 is configured to be adjustable with respect to the longitudinal axis of the screw assembly 150. For instance, the coupling assembly 110 is configured to be pivotally, rotationally and angularly adjustable with respect to the screw assembly 150, including the longitudinal axis thereof. The various components of the anchoring system 100 may be made of a material such as, for example, stainless steel, titanium, titanium-alloy, or the like.

FIGS. 2A-2C show various views of a non-limiting embodiment of the coupling assembly 110. As seen, the coupling assembly 110 includes a coupling body 112, a saddle 114, and a clamp 116. The coupling body 112 includes two upwardly extending arms 1122 that extend longitudinally in a superior direction. The coupling body 112 has a pair of slots 1123 configured to receive an elongate rod (not shown). As seen, the coupling body 112 may have a "tulip" shape. The extending arms 1122 have an interior, an exterior, and upper surfaces. The coupling body 112 is configured to receive and hold a cap (not shown) in a predetermined location in the longitudinal direction after insertion in the coupling body 112, so that a bottom surface of the cap contacts and presses upon a surface of the elongate rod to hold the rod in a fixed position, preventing the rod from moving rotationally or longitudinally along the longitudinal axis of the rod. The coupling body 112 includes a cap retaining mechanism, as is known by those skilled in the art, such as, for example, a tongue and grove mechanism, a threading, or the like, to engage the cap and hold it fixedly in the predetermined location in the coupling body 112.

As the cap (not shown) is inserted (e.g., rotated from a first position to a second position), the coupling body may include stops (not shown) or other limiting mechanisms to prevent the cap from moving past a certain point and/or from moving back (e.g., rotating back) from a predetermined engaged position whereby the cap exerts a force on the rod, as is known by those skilled in the art.

The coupling body 112 is configured to receive and fixedly hold the saddle 114 and clamp 116. The inner wall of the coupling body 112 may include a protrusion (e.g., tongue) or a recess (e.g., grove) that may be configured to engage a corresponding recess (e.g., grove) or protrusion (e.g., tongue) provided on the saddle 114, so as to engage and hold the saddle 114 in a predetermined location in the coupling body 112. As seen in FIG. 2C, the saddle 114 may include a recess in a perimeter wall 1146. As noted earlier, the coupling body 112 may have any other cap retaining mechanism, including, but not limited to, a threading, as understood by those skilled in the art.

As seen in FIG. 2C, the saddle 114 includes an annular body that has an upper surface 1142, a lower surface 1144 and the perimeter wall 1146. The saddle 114 is configured to be inserted into and retained in the coupling body 112 (e.g., as seen in FIGS. 2B, 5C-5E). The upper surface 1142 may be shaped to match the shape of the elongate rod, thereby providing a substantially snug, contoured fit for the rod against the upper surface 1142. The matching shape of the upper surface 1142 helps to provide for a more compact coupling body 112 that provides for improved rigidity of the elongate rod when the rod is secured in the coupling body 112 by the cap. The outer surface of the perimeter wall 1146 is configured to contact an inner wall surface of the coupling body 112, as seen in FIGS. 5C-5D. The lower surface 1144 may include a lip portion 1145 formed by the perimeter wall, as seen in FIGS. 5C and 5D. The lip portion 1145 is configured to fasten to a corresponding lip portion 1162 of the clamp 116, as seen in FIGS. 5C and 5D.

The clamp 116 includes an upper portion 1161, a lower portion 1164, and an annular wall 1166. The upper portion 1161 includes the lip portion 1162. The lip portion 1162 may be pushed and snapped into the lower portion of the saddle 114, snapping into place and engaging the lip portion 1145 of the saddle 114, as seen in FIG. 5B. Alternatively, the saddle 114 may be pushed and the lower lip portion 1145 snapped onto the lip portion 1162 of the clamp 116. The annular wall 1166 has an outer surface and an inner surface. The inner surface may include an internal helical thread 117 formed on an inner circumference of the annular wall 1166, as seen in FIGS. 2A-2B. The thread 117 may be configured to engage a corresponding thread 1342 on the head portion 134 of the screw 130, as illustrated, for example, in FIG. 3C.

Referring back to FIGS. 2A-2C, the coupling assembly 110, including the coupling body 112, saddle 114 and clamp 116, may be selectively mounted to the screw assembly 150, as illustrated in FIG. 1. The coupling assembly 110 is configured to allow for adjustment, replacement or modification of specific components of the coupling assembly 110 or screw assembly 150 without removal of the screw 130 from the bone.

Figure 3C:
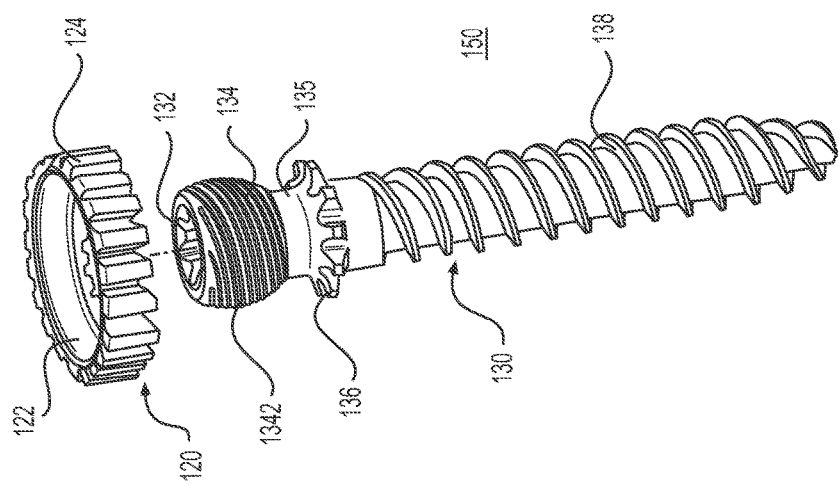
FIGS. 3A-3C show various views of an exemplary screw assembly that may be included in the anchoring system of FIG. 1.
Figure 3A:
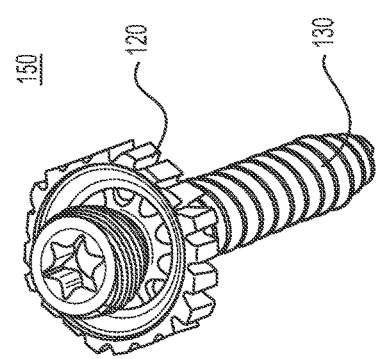
Figure 3B:
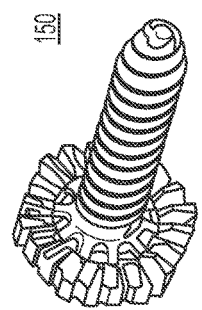

FIGS. 3A-3C show various views of an exemplary embodiment of a screw assembly 150 that may be included in the anchoring system 100 (shown in FIG. 1). As seen in FIGS. 3A-3C, the screw assembly 150 includes a screw 130 and a boring ring 120. The screw 130 has a head portion 134, a neck portion 135, an interface portion 136, and a shaft portion 138. The neck portion 135 is located between the head portion 134 and interface portion 136. The neck portion 135 may have a radial inward shape, as seen in FIG. 3C.

Figure 3E:
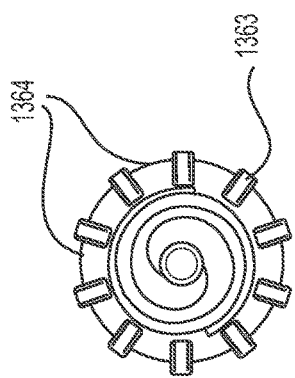
FIGS. 3D-3F show various views of an exemplary screw that may be included in the screw assembly of FIGS. 3A-3C.
Figure 3F:
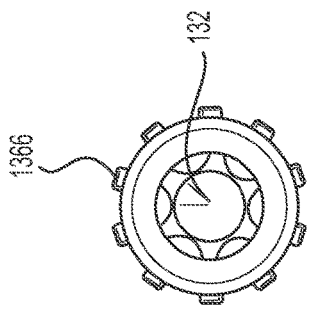
Figure 3D:
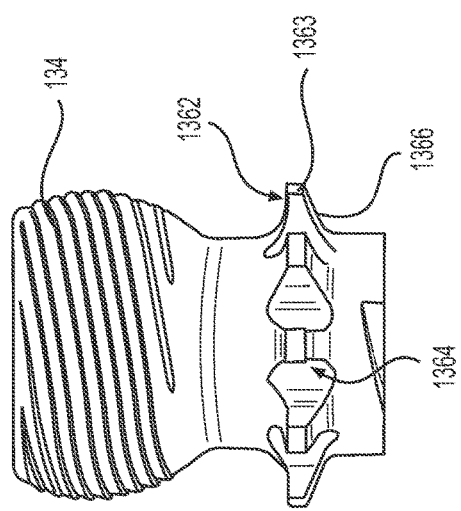

FIGS. 3D-3F show various detailed views of the screw 130. The head portion 134 may have a spherical shape. The head portion 134 includes a thread 1342 on the circumference that is configured to engage the thread 117 in the clamp 116 (shown in FIG. 2A). The head portion 134 may include a tool receptacle 132 at its distal end that is configured to receive a tool (e.g., shown in FIG. 7F). The tool receptacle 132 may have a hexagon shape, a torque-screw shape, or any other shape that may facilitate the screw 130 being driven into a bone by a tool, such as the screw driver 210 (shown in FIG. 6A).

Referring to FIG. 3C, the shaft portion 138 may have a thread that is adapted to be screwed into a bone, such as, for example, a vertebrae. However, alternative formations may be formed in the shaft portion 138 which provide the intended purposes of securing the screw 130 within a bone, as described herein. The shaft 138 may have a tapered shape, which may be provided with a high pitch thread. It is noted that the length, diameter, thread pitch, and thread diameter ratio of the shaft 138 may be selected based on the particular application of the screw 130, as understood by those skilled in the art.

Referring to FIG. 3D, the interface portion 136 may include a plurality of interface elements 1363 extending outwardly from the screw 130. The interface elements 1363 are configured to cut tissue and bone. The interface portion 136 may include by-pass channels (or graft windows) 1364 between each of the interface elements 1363. The interface portion 136 may also include a boring ring interface surface 1362 and a bone-facing surface 1366. The boring interface surface 1362, which may be formed by the upper surface of the interface elements 1363, can be tapered, thereby facilitating proper seating of the boring ring 120 atop of the interface elements 1363. The bone-facing surface 1366 may be tapered. The interface elements 1363 may include sharp cutting edges on the bone-facing surface 1366 side.

The interface portion 136 is located adjacent to the neck portion 135 and shaft 138, and configured to receive fibrous tissue, blood, and bone from the cutting teeth 128 of the boring ring 120 (shown in FIGS. 4A-4C) via the by-pass channels 1364 as the screw 130 is advanced into bone. The interface portion 136 is further configured to receive and guide fibrous tissue, blood, and bone from the cutting edges of the interface elements 1363. The interface portion 136 guides the fibrous tissue, blood, and bone inward and upward to the neck portion 135 via the by-pass channels 124 on the boring ring (see FIG. 3C) and the by-pass channels 1364 (see FIG. 3D). FIG. 3E shows a bottom view of the screw 130 and FIG. 3F shows a top view of the screw 130, including the radially extending interface elements 1363.

FIGS. 4A-4F shows various views of an exemplary embodiment of the boring ring 120 that is included in the screw assembly 150.

Figure 4C:
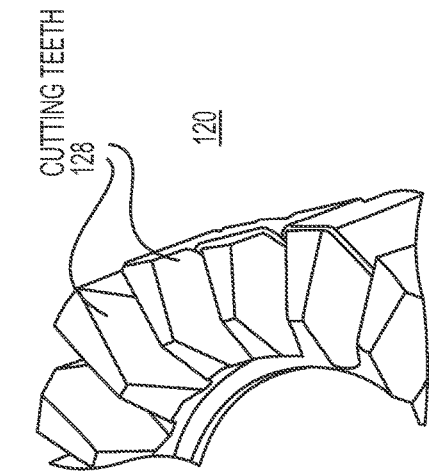
FIGS. 4A-4F shows various views of an exemplary boring ring that may be included in the screw assembly of FIGS. 3A-3C.
Figure 4A:
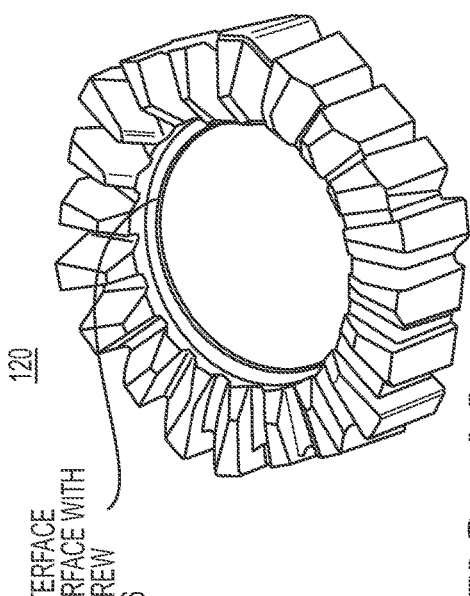
Figure 4B:
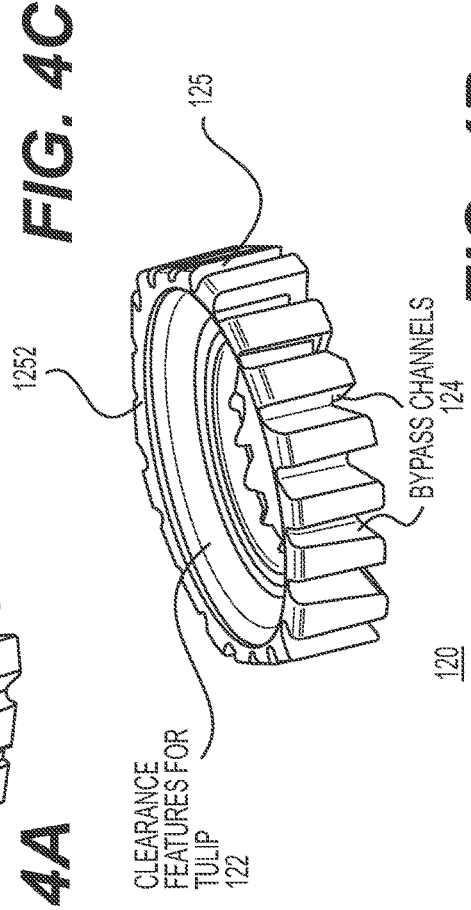
Figure 4D:
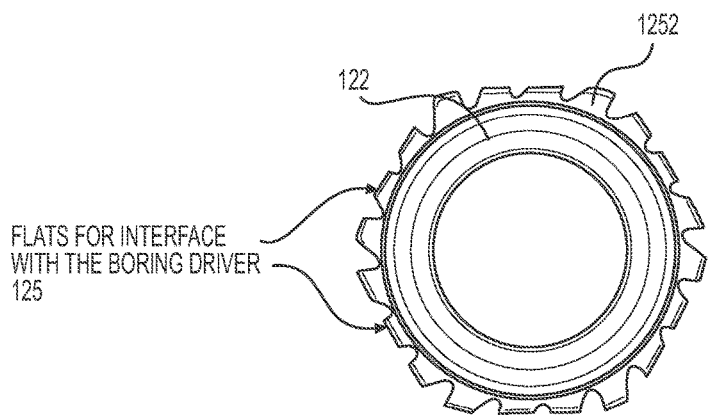
Figure 4E:
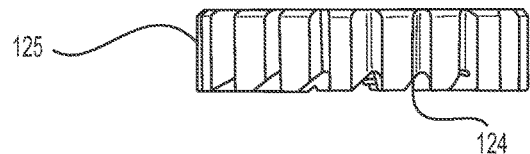

Referring to FIGS. 4A-4F, the boring ring 120 has a lower portion (shown in FIG. 4F), a wall portion 125 (shown in FIG. 4B) and an upper portion (shown in FIG. 4D). The lower portion may include an interface seating surface 126 and cutting teeth 128, as seen in FIG. 4A. The outer circumference of the interface seating surface 126 is greater than the outer circumference of the interface portion 136 of the screw 130 so as to provide a seating area for the interface elements 1363. The interface seating surface 126 may be substantially flat or slightly pitched to match the tapering angle of the boring ring interface surface 1362 of the interface elements 1363. The interface seating surface 126 is configured to contact and rest atop the interface elements 1363 (shown in FIGS. 3A-3C). The interface seating surface 126 may have a depth (or height) that is substantially the same as the height of the distal ends of the interface elements 1363, as illustrated in FIG. 5A. It is noted that the depth of the interface seating surface 126 may be greater or less than the height of the distal ends of the interface elements 1363.

The cutting teeth 128 are configured to cut fibrous tissue and bone (e.g., cortical bone) as the boring ring 120 is rotated during driving of the anchor assembly 100 into bone. The boring ring 120 may include a plurality of by-pass channels 124 formed between the cutting teeth 128, as illustrated in FIGS. 4A-4C. The cutting teeth 128 may be configured to facilitate movement of tissue, blood and bone from the cutting surfaces into the by-pass channels 124 and inward toward the neck portion 135 of the screw assembly 150, as illustrated at 810 in FIGS. 8G-8H. As illustrated in FIGS. 7G-7H, the width of the by-pass channels 1364 in the interface portion 136 may be greater than the width of the by-pass channels 124 in the boring 120.

Figure 4F:
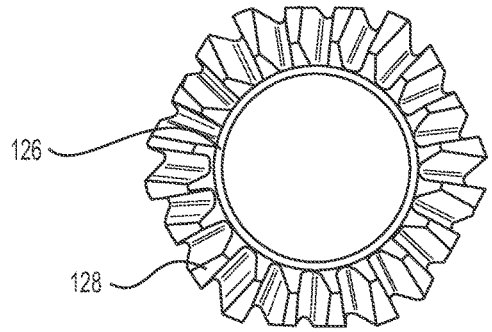

The wall portion 125 of the boring ring 120 includes a plurality of teeth along the wall perimeter, with a by-pass channel 124 disposed between each of the cutting teeth 128. Referring to FIGS. 4D and 4F, the wall portion 125 may have one or more flat portions that are configured to interface with a boring driver 220, as illustrated in FIGS. 7G-7H. In the embodiment illustrated in FIG. 4D, the wall portion 125 may be formed in the shape of a hexagon, with six flat portions. It is noted that the wall portion 125 may have any number of flat portions that interface with a corresponding boring driver, and the shape of the wall portion 125 is not limited to a hexagon shape, but may have any other shape as those skilled in the art would recognize which would provide the intended purposes of the disclosure as described herein.

Figure 8B:
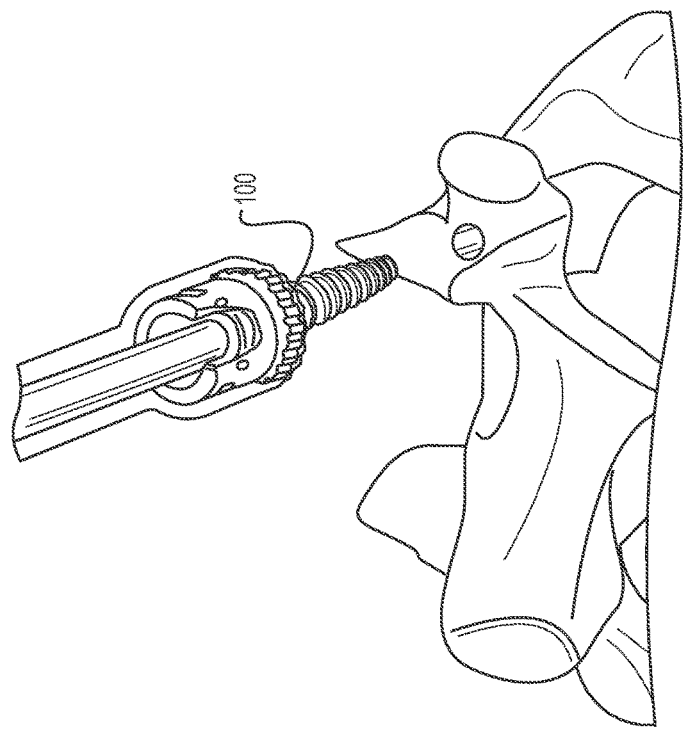
FIGS. 8A-8H show various stages of implanting the exemplary anchoring system of FIG. 1 into a bone.
Figure 8A:
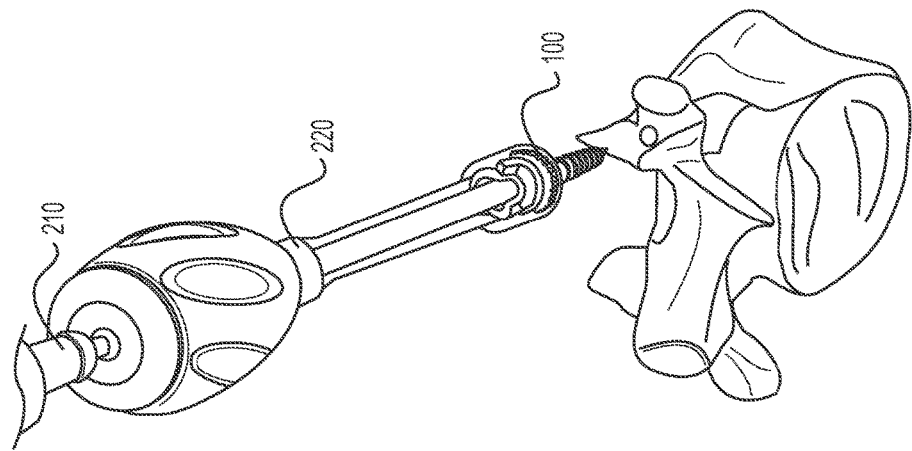

The upper portion of the boring ring 120 (shown in FIGS. 4B and 4D) may include an annular portion 122 that is configured to provide clearance for the coupling body 112 (shown in FIGS. 5A-5E) and a seating portion 1252. The annular portion 122 may be provided with a smooth, low-friction surface that facilitates polyaxial angulation, pivoting, and rotation of the coupling assembly 110 with respect to the screw assembly 150, as illustrated in FIGS. 5C-5E. The annular portion 122 may include a radially-shaped surface that is configured to enhance collection and retention of tissue, blood and bone to facilitate bone growth, as illustrated in FIG. 8H. The surface of the annular portion 122 may have other shapes, including, for example, but not limited to, a tapered shape, an L-shape, or the like. The shape of the annular portion 122 may depend on the shape of the coupling body 112, as those skilled in the art would recognize.

Referring to FIG. 4B and FIG. 5B, the outer circumference of the seating portion 1252 is greater than the outer circumference of the portion of the coupling body 112 (see FIG. 2C) that may contact the annular portion 122, to avoid obstructing movement of the coupling assembly 110 with respect to the screw assembly 150.

Figure 8C:
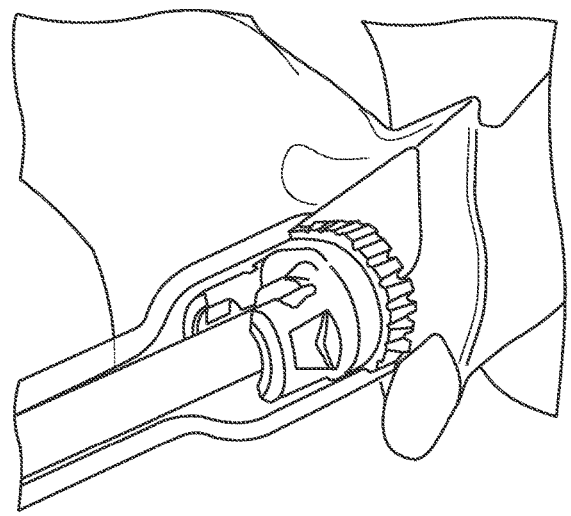
Figure 8D:
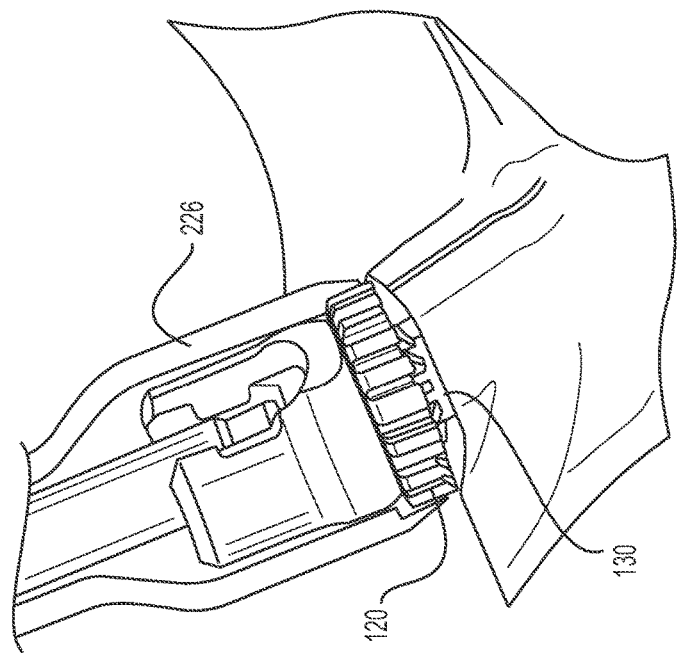
Figure 8F:
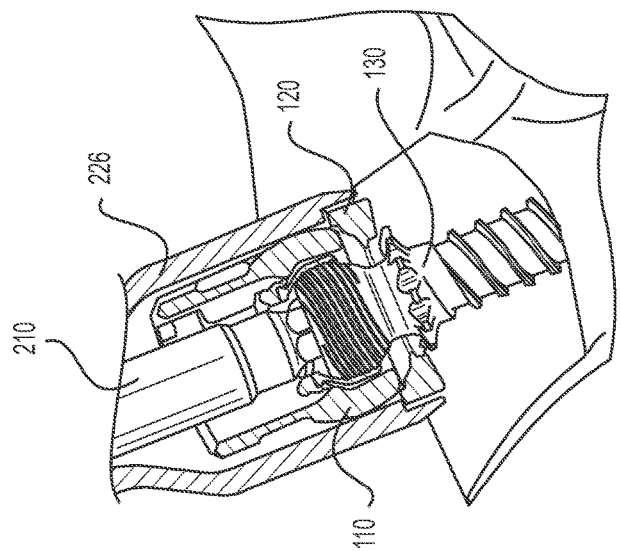
Figure 8E:
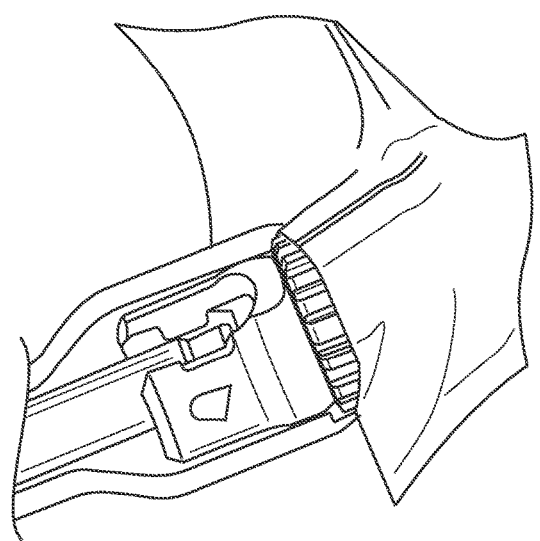
Figure 8H:
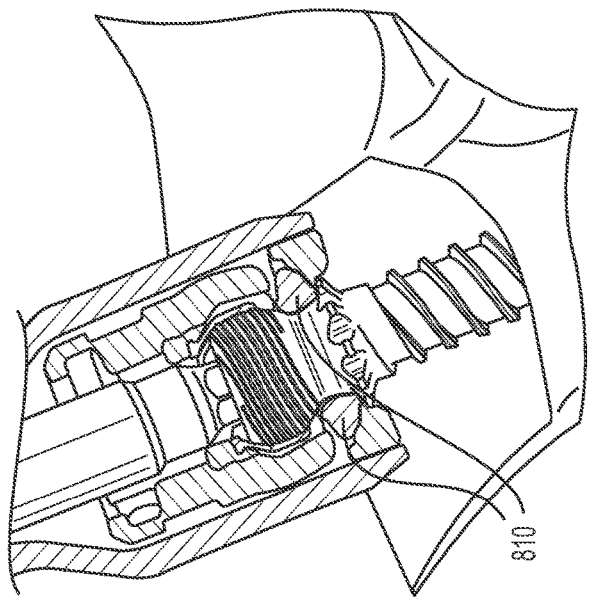

When the anchor assembly 100 is driven into bone, the longitudinal axis of the coupling assembly 110 may be aligned with the longitudinal axis of the screw assembly 150, and the boring ring 120 may be biased in a substantially orthogonal position by the contact surface of the lower portion of the coupling assembly 110 (shown in FIG. 5B) and the engaging interface of the boring driver (shown in FIGS. 8C-8D). This configuration assists with optimal anchoring of the anchoring system 100 into bone, providing maximum surface contact between the lower portion of the ring 120, coupling assembly 110 and bone.

Figure 8G:
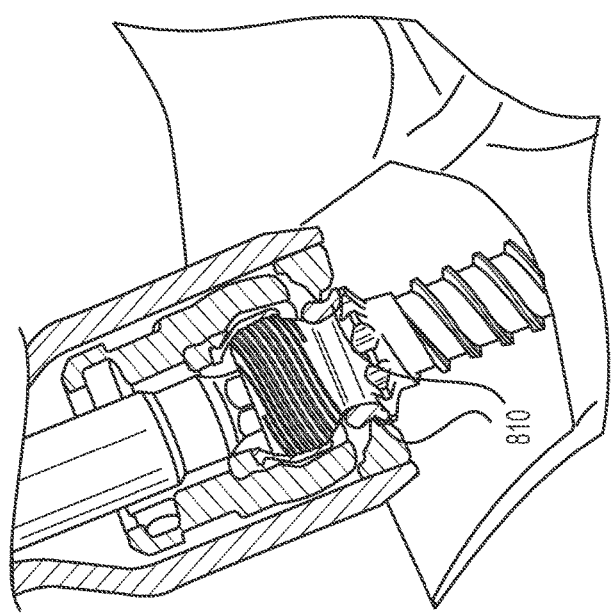

As seen in FIGS. 5A-5E, the coupling assembly 110 may be pivotally, rotationally and angularly adjustable with respect to the screw assembly 150. Furthermore, the boring ring 120 may be configured to float along the longitudinal axis of the screw assembly 150, moving (or floating) between the interface portion 136 of the screw 130 and the lower portion of the coupling assembly 110, as seen in FIGS. 5A and 5B, respectively. The floating configuration of the boring ring 120 facilitates enhanced, inward, upward and radial movement of tissue, blood and bone about the neck portion 135 of the screw 130, between the coupling assembly 110 and interface portion 136 of the screw 130. The tissue, blood and bone that is forced up through the by-pass channels and located around and in the anchoring system 100 generates a form of bone graft, as seen in FIGS. 8G-8H.

After insertion of the anchor system 100 in bone (e.g., as seen in FIGS. 8A-8H), the coupling assembly 110 may be pivoted, rotated, and/or angularly adjusted to a desired position, as seen in FIGS. 5C-5E, to allow for proper rod alignment and placement. As illustrated in FIGS. 9A-9B, graft material may be left inside the by-pass channels 124 of the boring ring 120, including the outer by-pass channels 124 of the wall portion 125, as illustrated at 820 in FIG. 9B.

Figures 6A, 6B, 6C:
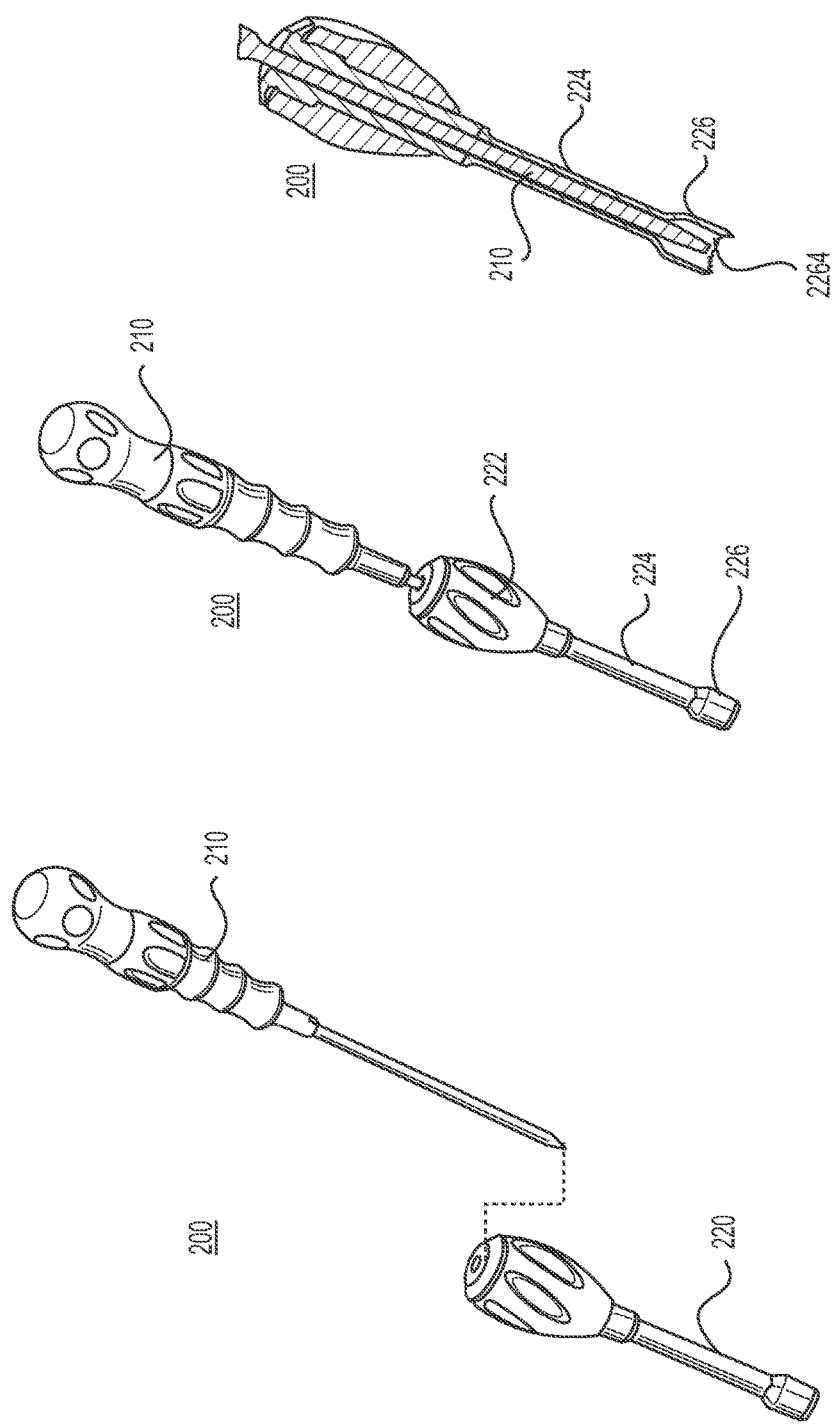
FIGS. 6A-6C show various views of an exemplary embodiment of a driver assembly that may be used with the anchoring system in FIG. 1.

FIGS. 6A-6C show various views of the driver assembly 200 that may be used with the anchoring system 100 (shown in FIG. 1). The driver assembly 200 may include a screw driver 210 and a boring driver 220. The screw driver 210 and boring driver 220 may be used separately. The boring driver 220 may include a longitudinal channel as seen in FIG. 6C that is configured to receive and guide the screw driver 210 to engage the head portion of a pedicle screw, as discussed below.

Figure 7D:
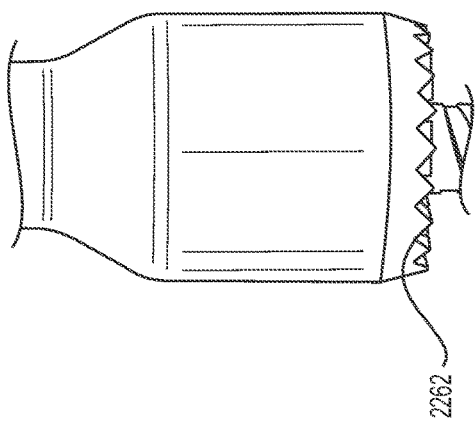
Figure 7E:
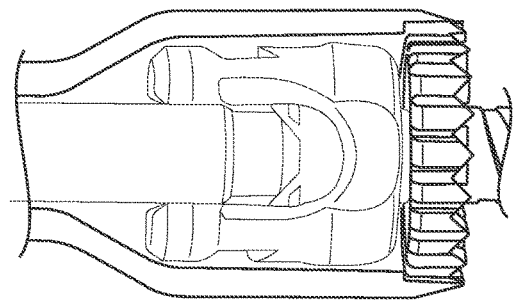

FIGS. 7A-7H illustrate various views of the boring driver 220. Referring to FIG. 7A, the boring driver 220 may include a handle 222, a driver shaft 224, and a driver head 226. The driver head 226 may include teeth (or serrations) 2262 at its distal end, which are configured to cut into tissue and bone. As seen in FIGS. 7B and 7C, the driver head 226 may have a cavity 2264 that is configured to receive the coupling assembly 110 and boring ring 120 (shown in FIGS. 8G-8H). The driver head 226 may also include a plurality of engaging interfaces that are configured to contact and engage the corresponding flat portions of the ring 120 (shown in FIG. 4A), thereby engaging and substantially locking the boring ring 120 in place with respect to the driver head 226, so that when the handle 222 is turned under force of hand and the driver head 126 rotates resultantly, the boring ring 120 is caused to rotate simultaneously. For example, the driver head 226 may have six engaging interfaces that engage the six corresponding flat portions of the boring ring 120.

As illustrated in FIGS. 7D-7H, driver head 226 may be configured to envelope the entirety of the coupling assembly 110 and the boring ring 120. The driver head 226 may include a ring stop 2266 (shown in FIG. 7F) to prevent the boring ring from going too deep into the cavity 2264 and to maintain the boring ring 120 in an optimal position to cut into bone by exposing the entirety (or a portion) of the cutting teeth on the lower portion of the boring-ring 120. The driver head 226 may be configured to allow the boring ring 120 to float along the longitudinal axis of the screw assembly 150.

As noted earlier, the boring driver 220 may include a longitudinal channel along the entire length of the boring driver 220. The channel may be positioned centrally along the longitudinal axis of the boring driver 220. The channel may be configured to receive and guide the head and shaft portion of the screw driver 210 to the driver head 226, so as to engage and drive the receptacle 132 in the head portion of the screw 130 when driving the anchoring system 100 into bone.

FIGS. 8A-8H illustrate various stages of implanting the anchoring system 100, according to principles of the disclosure, which will be referred to herein to describe a non-limiting example of an application of the disclosure.

After a surgical area is cleaned on the patient, an incision is made, the muscle tissue is moved to the side(s), and other common surgical procedures are carried out, tracks for the pedicle screws may be prepared. In this regard, hard bone surface may be removed and a guide track may be inserted under x-ray guidance into the pedicle of the vertebrae. The depth and position of the guide track may be checked. Then a thread is tapped into the bone for the anchoring system 100. The process would be repeated for each implant of the anchoring system 100.

Figure 7F:
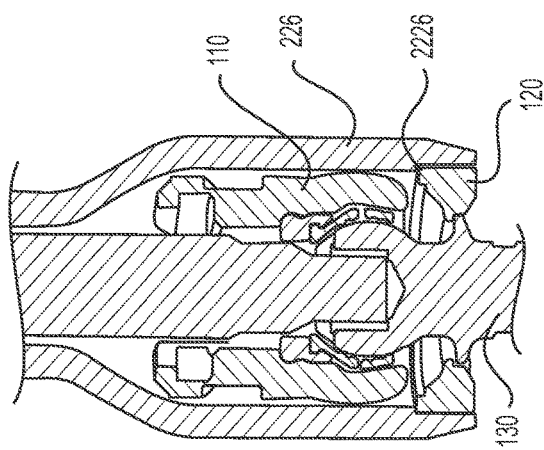

Referring to FIG. 7F, the anchoring system 100 may be placed in the driver head 226 of the boring driver 220 and the head and shaft of the screw driver 210 inserted into the channel of the boring driver 220. The screw driver 210 may be moved downward and manipulated until the screw driver 210 head is sufficiently seated in and engaged with the screw head 134 to ensure a secure connection. The driver assembly 200, including the anchoring system 100, can then be aligned with the tap in the bone, as illustrated in FIGS. 8A and 8B, and screwed into the threaded tap in the bone using the driver assembly 200. Through manipulation of one or both of the handles on the screw driver 210 and boring driver 220, the surgeon may selectively drive the screw 130 into the bone and/or the boring ring 120 and boring driver head 226 to cut tissue and/or bone.

For instance, referring to FIGS. 8G and 8H, the surgeon may advance the screw 130 into the bone tap by turning the handle of the screw driver 210 and then switching over and turning the handle of the boring driver 220 to drive the boring driver head 226 and boring ring 120 to cut into bone and move the boring ring 120 from the position shown in FIG. 8G to the position shown in FIG. 8H.

Once the anchoring system 100 is implanted in the desired position, the screw driver 210 may be removed and the coupling assembly 110 may be pivoted, angularly adjusted, or rotated. The coupling assembly 110 may be manipulated by, for example, retracting the boring driver 220 until the boring ring 120 is completely free of the boring driver head 226 and then manipulated to position the coupling assembly 110 in the desired position and angle. This process is repeated for each pedicle screw before the rest of the surgical procedure is carried out, including rod placement.

Figure 9D:
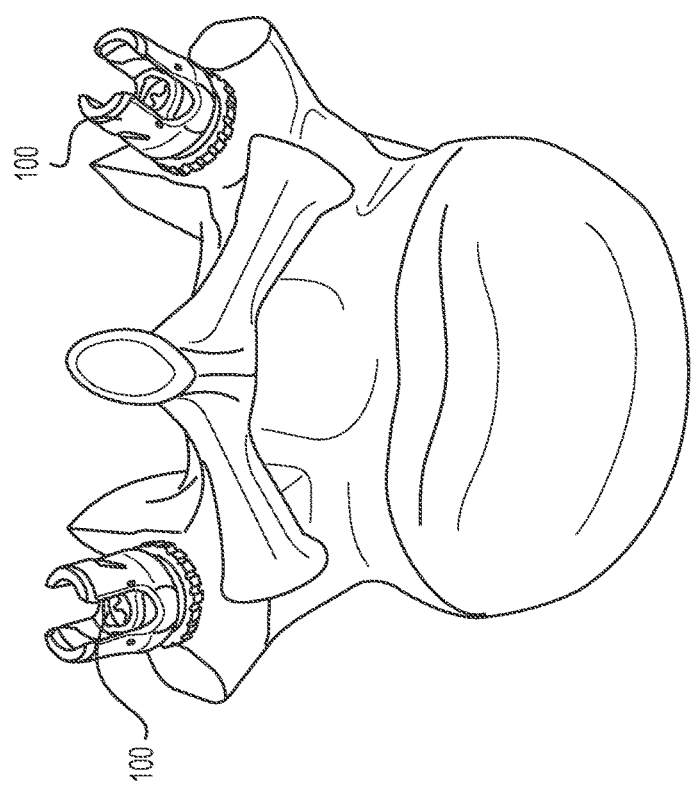

FIGS. 9A-9D show various views of the anchoring system 100 after it has been implanted in bone. FIGS. 9A and 9B show a cross-section cut view and a side view, respectively, of the anchoring system 100 after the boring driver 220 and screw driver 210 (shown in FIG. 8A) are removed. As seen in FIGS. 9A and 9B, the graft material may be left inside the by-pass channels 124 of the boring ring 120, including the outer by-pass channels of the wall portion 125, as seen at 820 in FIG. 9B, to promote graft formation.

Figure 9C:
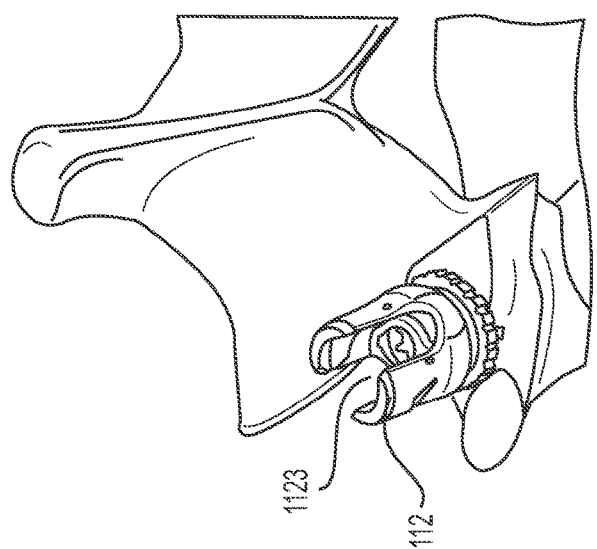

FIG. 9C shows a partial view of a completed placement of the anchoring system 100 in a pedicle of the vertebra. FIG. 9D shows a perspective, substantially complete view of the vertebra with completed placement of the anchoring system 100 in both of the pedicles of the vertebra. As seen in FIGS. 9C and 9D, the coupling assemblies 110 of the anchoring systems 100 may be positioned so that the slots 1123 of the coupling bodies 112 are aligned with the slots of coupling bodies (not shown) of anchoring systems located on an adjacent vertebra (not shown). The anchoring systems of the pair of vertebrae may then be cross-connected using, for example, elongate rods, and the rods may be locked in place by, for example, caps screwed into each of the coupling assemblies, as is known in the art.

The terms "including," "comprising," and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

What is claimed is:

1. An anchoring system comprising:
    a screw system comprising:
        a screw including a screw head, a screw shaft and a plurality of interface elements, each pair of the interface elements having an interface by-pass channel located therebetween;
        a boring ring including an upper surface, a lower surface, a wall portion extending between the upper surface and the lower surface, and a plurality of cutting teeth along the wall portion extending longitudinally from the upper surface to the lower surface; and
        a coupling assembly that is adjustable with respect to a longitudinal axis of the screw, the coupling assembly being adapted to attach to the screw head; and
        a driver comprising a handle, a driver shaft, and a driver head having a cavity configured to receive the coupling assembly and the boring ring,
        wherein the driver head includes teeth at its distal end configured to cut into tissue and bone.

2. The anchoring system of claim 1, wherein the driver head includes a plurality of engaging interfaces that are configured to contact and engage corresponding flat portions of the boring ring.

3. The anchoring system of claim 1, wherein the driver head includes a ring stop to prevent the boring ring from recessing too deep into the cavity.

4. The anchoring system of claim 1, wherein the coupling assembly comprises a coupling body that receives and holds an elongate rod and a clamp that couples the coupling body to the screw head.

5. The anchoring system of claim 4, wherein the coupling assembly further comprises a saddle that attaches to the clamp.

6. The anchoring system of claim 1, wherein the plurality of interface elements extend radially from the screw in a direction that is substantially normal to the longitudinal axis of the screw.

7. The anchoring system of claim 1, wherein the plurality of interface elements comprise a tapered surface.

8. The anchoring system of claim 1, wherein the screw further includes a neck portion located between the screw head and the plurality of interface elements.

9. The anchoring system of claim 8, wherein the neck portion is configured to receive tissue, blood and bone to promote graft formation.

10. The anchoring system of claim 1, wherein the boring ring is configured to float between the plurality of interface elements and the coupling assembly.

11. The anchoring system of claim 1, wherein the boring ring includes an annular portion that facilitates polyaxial angulation, pivoting and rotation of the coupling assembly.

12. An anchoring system comprising:
a screw assembly comprising:
a screw including a screw head and a plurality of interface elements;
a boring ring including an upper surface, a lower surface, a wall portion extending between the upper surface and the lower surface, and a plurality of cutting teeth along the wall portion extending longitudinally from the upper surface to the lower surface; and
a coupling assembly that attaches to the screw head, wherein the boring ring is positioned between the plurality of interface elements and the coupling assembly; and
a driver comprising a handle, a driver shaft, and a driver head having a cavity configured to receive the coupling assembly and the boring ring,
wherein the driver head includes teeth at its distal end configured to cut into tissue and bone.

13. The anchoring system of claim 12, wherein the driver head includes a plurality of engaging interfaces that are configured to contact and engage corresponding flat portions of the boring ring.

14. The anchoring system of claim 12, wherein the driver head includes a ring stop to prevent the boring ring from recessing too deep into the cavity.

15. The anchoring system of claim 12, further comprising a by-pass channel disposed between each adjacent pair of the plurality of interface elements.

16. The anchoring system of claim 12, wherein the coupling assembly comprises a coupling body that receives and holds an elongate rod, a clamp that attaches the coupling body to the screw head, and a saddle that attaches to the clamp.

17. The anchoring system of claim 12, wherein the plurality of interface elements extend radially from the screw in a direction that is substantially normal to a longitudinal axis of the screw.

18. The anchoring system of claim 12, wherein the screw further includes a neck portion located between the screw head and the plurality of interface elements.

* * * * *